(12) United States Patent
Mueller-Pathle (10) Patent No.: US 10,363,367 B2
(45) Date of Patent: Jul. 30, 2019

(54) FILLING DEVICE FOR A DRUG DELIVERY DEVICE AND SYSTEM WITH A FILLING DEVICE AND DRUG DELIVERY DEVICE

(71) Applicant: Sanofi-Aventis Deutschland GmbH, Frankfurt am Main (DE)

(72) Inventor: Stephan Mueller-Pathle, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/778,581

(22) PCT Filed: Mar. 27, 2014

(86) PCT No.: PCT/EP2014/056107
§ 371 (c)(1),
(2) Date: Sep. 19, 2015

(87) PCT Pub. No.: WO2014/154777
PCT Pub. Date: Oct. 2, 2014

(65) Prior Publication Data
US 2017/0043090 A1    Feb. 16, 2017

(30) Foreign Application Priority Data
Mar. 28, 2013    (EP) .................................... 13161516

(51) Int. Cl.
*A61J 1/20*        (2006.01)
*A61M 5/20*     (2006.01)
(Continued)

(52) U.S. Cl.
CPC .......... *A61M 5/1782* (2013.01); *A61J 1/2096* (2013.01); *A61M 5/14244* (2013.01); *A61M 5/2033* (2013.01); *A61M 2209/045* (2013.01)

(58) Field of Classification Search
CPC .......... A61M 5/204; A61M 2005/3114; A61M 2209/04; A61M 2209/045;
(Continued)

(56) References Cited

U.S. PATENT DOCUMENTS 5,779,676 A * 7/1998 Kriesel ................. A61M 5/152
604/132
5,845,600 A * 12/1998 Mendes .................... A01K 7/02
119/51.5
(Continued)

FOREIGN PATENT DOCUMENTS

CN        201418926 Y       3/2010
WO        0152990 A1        7/2001
(Continued)

OTHER PUBLICATIONS

Definition of Pump from Dictionary.com (Nov. 15, 2017).*

*Primary Examiner* — Laura A Bouchelle
*Assistant Examiner* — Dung T Ulsh
(74) *Attorney, Agent, or Firm* — McCarter & English, LLP (57) ABSTRACT

The present invention relates to a filling device for filling a reservoir, the filling device comprising a housing configured to hold a container for a liquid; a conduit arranged for fluid engagement with the container; a drive unit configured to expel a liquid from the container through the conduit; and a connector configured to be attachable to a reservoir, wherein the connector comprises at least one contact element; the filling device further comprising a trigger assembly arranged to act on the drive unit such that when the trigger assembly is activated the liquid is expelled from the container through the conduit.

15 Claims, 2 Drawing Sheets
Specification includes a Sequence Listing.

(51) Int. Cl.
   *A61M 5/142* (2006.01)
   *A61M 5/178* (2006.01)
(58) Field of Classification Search
   CPC .. A61M 2205/3379; A61M 2205/3389; A61M 2039/1005; A61M 2039/1022; A61M 5/1782; A61J 1/20; A61J 1/2003; A61J 1/2096; A61J 1/22; A61J 2200/76; B65B 3/003; B65B 3/26; B65B 3/30; B65B 3/12
   See application file for complete search history.

(56) References Cited

U.S. PATENT DOCUMENTS

| | | | | |
|---|---|---|---|---|
| 6,062,166 | A * | 5/2000 | Macrina | A01K 7/02 119/51.11 |
| 6,293,159 | B1 * | 9/2001 | Kriesel | G01P 13/0026 604/133 |
| 6,453,927 | B1 * | 9/2002 | Peterson | G05D 7/0682 137/3 |
| 7,281,494 | B1 * | 10/2007 | Connerley | A01K 7/02 119/74 |
| 7,637,897 | B2 * | 12/2009 | Ginggen | A61M 5/14276 604/288.01 |
| 8,298,171 | B2 | 10/2012 | Ishikawa et al. | |
| 8,303,535 | B2 | 11/2012 | Both et al. | |
| 8,568,361 | B2 * | 10/2013 | Yodfat | A61M 5/1413 604/152 |
| 2005/0209569 | A1 | 9/2005 | Ishikawa et al. | |
| 2006/0089619 | A1 * | 4/2006 | Ginggen | A61M 5/14276 604/891.1 |
| 2008/0035241 | A1 * | 2/2008 | Wittbold | A01K 7/06 141/361 |
| 2009/0082757 | A1 | 3/2009 | Rogers et al. | |
| 2009/0143732 | A1 * | 6/2009 | O'Connor | A61M 5/14248 604/151 |
| 2009/0163865 | A1 * | 6/2009 | Hines | A61M 5/14216 604/131 |
| 2009/0275888 | A1 * | 11/2009 | Kriesel | A61M 5/14244 604/86 |
| 2009/0275896 | A1 * | 11/2009 | Kamen | G05D 7/0647 604/151 |
| 2009/0275916 | A1 * | 11/2009 | Harms | A61M 5/24 604/506 |
| 2010/0125246 | A1 * | 5/2010 | Kalpin | A61M 5/14276 604/151 |
| 2010/0243667 | A1 * | 9/2010 | Keyes | B65B 3/28 221/1 |
| 2011/0108158 | A1 * | 5/2011 | Huwiler | A61M 5/14244 141/2 |
| 2011/0130742 | A1 * | 6/2011 | Hawkins | A61M 5/14248 604/500 |
| 2011/0132490 | A1 * | 6/2011 | Kuhni | A61J 1/20 141/7 |
| 2011/0160655 | A1 * | 6/2011 | Hanson | A61M 5/1413 604/67 |
| 2011/0295205 | A1 * | 12/2011 | Kaufmann | A61M 5/3287 604/136 |
| 2012/0259283 | A1 * | 10/2012 | Haase | A61M 5/14276 604/151 |
| 2012/0289900 | A1 * | 11/2012 | Chong | A61M 5/00 604/113 |
| 2012/0315163 | A1 * | 12/2012 | Yan | F04B 19/20 417/375 |
| 2013/0192391 | A1 * | 8/2013 | Bruehwiler | G01N 1/08 73/863.01 |
| 2013/0276531 | A1 * | 10/2013 | Benner | B60K 15/03 73/290 R |
| 2013/0296807 | A1 * | 11/2013 | Lintern | A61J 1/20 604/272 |
| 2014/0088509 | A1 * | 3/2014 | Sonderegger | A61M 25/02 604/157 |
| 2014/0191054 | A1 * | 7/2014 | Hingley | A61M 11/005 239/1 |
| 2015/0128617 | A1 * | 5/2015 | Mikheev | F25D 19/00 62/47.1 |
| 2015/0374907 | A1 * | 12/2015 | Morton | A61M 5/14546 604/111 |
| 2016/0266663 | A1 * | 9/2016 | Holsen | G06F 3/03545 |

FOREIGN PATENT DOCUMENTS

| | | | |
|---|---|---|---|
| WO | 2004004809 A1 | 1/2004 | |
| WO | 2009125398 A2 | 10/2009 | |
| WO | 2012019641 A1 | 2/2012 | |
| WO | WO 2012174612 A1 * | 12/2012 | ......... A61M 11/005 |
| WO | 2013/016363 A2 | 1/2013 | |

\* cited by examiner

FILLING DEVICE FOR A DRUG DELIVERY DEVICE AND SYSTEM WITH A FILLING DEVICE AND DRUG DELIVERY DEVICE

CROSS REFERENCE TO RELATED APPLICATIONS

The present application is a U.S. National Phase Application pursuant to 35 U.S.C. § 371 of International Application No. PCT/EP2014/056107 filed Mar. 27, 2014, which claims priority to European Patent Application No. 13161516.3 filed Mar. 28, 2013. The entire disclosure contents of these applications are herewith incorporated by reference into the present application.

FIELD OF INVENTION

The present invention relates to filling devices for a reservoir, in particular for a reservoir of a mobile infusion device.

BACKGROUND

Chronic diseases require administering of medicaments or drugs according to a predefined time schedule in order to keep the concentration level of a pharmaceutically active substance within given margins. Many medicaments require administration by way of infusion. Therefore, patients administering the medicament in self-medication typically make use of mobile infusion devices or pump devices, e.g. so called patch pumps. Such devices should be universally applicable and should be operable even by persons without formal medical training.

Moreover, such devices, like infusion pumps, should provide accurate, precise and reliable dosing and dispensing of the respective medicament. Typically, the medicament to be dispensed is provided in a disposable container, such as an ampoule or pouch. One type of patch pumps come in a modular design, e.g. comprising a disposable module comprising a reservoir and a reusable module comprising a pump mechanism. Once the medicament from the reservoir module is spent the device is decomposed, the empty reservoir module is disposed and a new reservoir module is reassembly with the reusable pump mechanism module. Another type of patch pumps come in a slightly different modular design. One module, the disposable module, comprising the reservoir and infusion mechanism the other module, the reusable module, comprising the control means for managing the pump's functions. As one example, the OmniPod system, comprises a reusable control module and a disposable module that does not contain medicament at once. Before the user attaches the disposable module to the infusion site, the reservoir is filled with medicament. The user, which, in most case will be the patient, has to withdraw medicament from a vial by means of a syringe and use this syringe to fill the reservoir through a fill port in the disposable module. This procedure, using a syringe to fill a reservoir of a mobile infusion device is well known in the art and used with different types of mobile infusion or pump devices.

For drug stability and sterility reasons the reservoirs of mobile infusion devices or pump devices, e.g. patch pumps, are delivered in an empty state. The medicament then has to be filled just before the reservoir is about to be used. Usually, a patient or a health care professional fills the reservoir with liquid medicament which comes in a vial or ampoule in a manner similar to what is described above.

However, from a safety and usability point of view this might not be the best solution as this procedure holds quite some risks. First the patient has to take care of the hygiene, ensuring that no contamination occurs during preparation of the syringe and during operating the syringe to first withdraw the liquid medicament and the dispense it into a reservoir. On top, he or she has to ensure that the medicament is the right medicament and correct concentration/dose and that the medicament is not deteriorated. Second, the patient has to make sure that the needle is put correctly into the filling port. Not correctly attaching the needle could for example lead to filling the medicament into the module body or housing instead of the reservoir. This would cause damage to the reservoir module and render it unusable. Another defect could be that the needle is inserted in a way that could damage the reservoir inside the module. Damaging the module could cause leaking of medicament during injection. In consequence, the patient would not be given the right dose or amount of medicament; however, no malfunction of the device is being detected. This seems to be a very critical risk. Third the patient needs to make sure that just about the right amount of medicament is filled. Overfilling may not only waste the precious medicament. It may also have a negative impact on the module's adhesive layer that is to ensure properly fixing the module to the body. Underfilling as the opposite, will cause the problem that the reservoir module is empty sooner as expected by the patient. This could get the patient in a precarious situation in case he or she does not have a replacement module or a refill ampoule and syringe at hand. Fourth the patient has to take care of needle stick injuries. Needle stick injuries constitute a severe risk in particular for health care professionals in view of diseases like, e.g., HIV, hepatitis B, asf. Fifth, a potential interruption during the filling procedure may endanger the whole process. The user might be interrupted by a phone call, some one ringing at the door, or some other incident catching his or hers attention. After returning the attention to the filling procedure the patient might find the syringe laying there for a couple of minutes. This could cause the risk of contamination, in particular when the syringe laid there unattendently. Sixth the user has to have the manual capabilities to handle syringes and ampoules in order to use this kind of devices. In particular withdrawing liquids from ampoules however requires some aptitude.

It is generally of importance, that the patient strictly follows a given prescription schedule. Therefore, it is necessary to have enough medicament at hand. However, as the medicament container is inside the pump device it may not be obvious for the user to ensure that the amount of medicament will be sufficient. Running out of medicine would put the patient of a chronic disease in a serious situation which may also be physically impacting.

It is therefore an object of the present invention to provide a filling device for a reservoir of a drug delivery device featuring an improved safety mechanism in order to minimize at least one of the risks associated with the filling procedure. It is a further object to provide intuitive and unambiguous support for a user in handling and/or to operating the drug delivery device when filling a liquid, e.g. medicament, into a reservoir of a drug delivery device. Furthermore, it is an objective to improve user comfort and safety in handling and/or operating the device. In particular, the invention serves to facilitate compliance with a given prescription schedule.

SUMMARY

According to a first aspect of the invention a filling device for filling a reservoir comprises a housing configured to hold a container for a liquid, a conduit arranged for fluid engagement with the container, a drive unit configured to expel a liquid from the container through the conduit and a connector configured to be attachable to a reservoir. The filling device further comprises a trigger assembly arranged to act on the drive unit such that when the trigger assembly is activated the liquid is expelled from the container through the conduit.

The connector of the filling device according to the invention further comprises at least one contact element. The at least one contact element may be configured to enable transmission of signals to and from the filling device.

Having a contact element in place could allow determining that, for example, the correct filling device is attached the pump device. This could improve safety in handling pump devices because a user can be prevented to mistakenly attach a wrong filling device to a pump.

A contact element may be provided mechanically or electronically or a combination thereof.

The at least one contact element may be configured to determine that the filling device is connected to a reservoir or pump device. In one example, the contact element comprises a peg that is movable from a first position when not attached to a reservoir to a second position when attached to a reservoir. Thereby, information is transmitted, that the filling device is attached to the reservoir. This mechanical transmission can be used to mechanically change a status indicator. Alternatively, the mechanical transmission may act on an electrical switch that changes the display of a status indicator.

Alternatively, the contact element may comprise one or more electrical contact.

In another example, the contact element comprises a peg that is fixed and arranged to engage with a corresponding indent at a reservoir when the filling device is attached to the reservoir. Thereby the connector is configured to identify a matching reservoir.

In another example the contact element comprises at least one electrical contact allowing signal transmission between the filling device and the pump device comprising the reservoir. Signals exchanged between the filling device and the pump system may comprise information about reservoir fill level, liquid type (e.g. medicament, solvent, or sterilization liquid), device type, e.g. When transmitting signals that comprise information about the device type, the connector is configured to identify a matching reservoir.

The contact element may further be arranged to move the conduit from a first state where is not in fluid communication with the container to a second state, where it is in fluid communication with the container. Hence, the liquid is in fluid communication with the conduit when the conduit is in fluid communication with the reservoir. Thereby it is ensured that the liquid is expelled into the reservoir.

In one embodiment, the contact element comprises a peg arranged on a movable hub that holds the conduit.

The liquid may comprise a ready to use drug or medicament. Alternatively, the liquid may comprise a solvent capable of reconstituting a lyophilized drug. Further alternatively, the liquid could comprise a solution capable of cleaning and/or sterilizing a medical device, preferably a pump device.

The container of the filling device according to the invention may be a cartridge. The cartridge may be generally cylindrical in shape. The cartridge may be made from glass. The cartridge may have a bung or stopper at one end. The cartridge may be sealed by a septum at the opposite end. The septum may be made from rubber.

The container may be replaceable.

The container of the filling device according to the invention may be a pouch, bellow, or other type of container that is flexible and/or compressible.

Alternatively, the filling device could comprise a prefilled syringe.

The connector of the filling device according to the invention may further comprise a sleeve arranged to permanently extend beyond the distal end of the conduit in distal direction. Thereby, the distal end of the conduit is shielded preventing a user to touch its distal end. Thereby, the distal end may be secured against damage. On the other hand, it may protect the user against injury when handling the filling device and inadvertently touching the distal end of the conduit. This is particularly useful, when the conduit has a sharp distal end, as according to one embodiment.

The drive unit of the filling device according to the invention may be implemented mechanically. A mechanically implemented drive unit may be activated manually. The mechanically implemented drive unit may require manual actuation to provide energy to expel the content from the container.

The drive unit of the filling device according to the invention may further comprise a stored-energy means configured to provide energy to expel the content from the container, wherein a trigger assembly is configured to activate the stored-energy means. The stored-energy means may be a spring, e.g. torsion spring, gas spring or rubber band. The stored-energy means provides the force necessary to expel liquid from the container.

Alternatively, the drive unit of the filling device may be implemented electro-mechanically. An electro-mechanically implemented drive unit may be activated manually, by a push button, a switch, or the like. The electro-mechanically implemented drive unit may further comprise a power source, e.g. battery, and a motor to provide force necessary to expel liquid from the container.

The drive unit of the filling device implemented either mechanically or electro-mechanically, may further comprise a controller. The controller may be configured to control the action of the drive unit. The drive unit of the filling device may be operated by the controller in expelling liquid from the container. The controller may be configured to stop the drive unit such that no liquid is expelled from the container. The drive unit may further comprise a contact connected to the controller to transmit a signal to the controller. The signal transmitted to the controller may command the controller to stop the drive unit such that no liquid is expelled from the container.

The conduit of the filling device according to the invention may further comprise a first state where it is not in fluid communication with the container and a second state, where it is in fluid communication with the container. When in the first state the liquid in the container is in sterile condition and protected against intrusion of bacteria, germs, dust, etc. When in the second state, the liquid can be expelled from the container.

The conduit of the filling device according to the invention may further be configured to establish a fluid communication with the reservoir.

According to an embodiment, the distal end of the conduit comprises a sharp end adapted to pierce a seal of the reservoir.

According to another embodiment, the conduit comprises a hollow needle cannula. The needle cannula may be in fluid communication with the container.

The sleeve of the filling device according to the invention may further be configured to mechanically connect to the reservoir. The sleeve may comprise a connector to releasably connect attach the filling device to the reservoir. When attached, the connection does not allow relative movement of the filling device and the reservoir along the axis of the conduit. Thereby, it is ensured that the conduit and the reservoir are in stable fluid communication. The mechanical connection also provides a guide to ensure that the conduit is properly connected to the reservoir.

For example, the sleeve may comprise a connector having a thread to releasably attach the filling device to the reservoir.

Alternatively, the sleeve of the filling device may comprise a bayonet-like connector, or a snap fit connector.

The connector of the filling device according to the invention may be configured to attach the filling device to a drug reservoir of a pump device. The connector may be adapted to connect to a matching connecting element. The matching connecting element may be part of a pump system comprising the reservoir.

The filling device may further comprise a display. The display may comprise single light or multiple lights, e.g. LED. The display may alternatively comprise an LCD or an electronic ink technology display.

The display may be configured to indicate a status of the filling device. The display of the filling device may be configured to indicate the status that the container of the filling device is empty. This may be indicated for example by a red light or a "STOP" sign.

The display may be configured to indicate that the filling device is attached to a reservoir. The display may be configured to indicate that the filling device matches the attached reservoir. This may be indicated for example by a green light or a "check" mark.

The display may be configured to indicate a malfunction of the filling device. This may be indicated by a blinking light, wherein the light is red, yellow, or orange, e.g.

According to a second aspect of the invention, a system comprises a filling device according to the invention and a pump device, wherein the pump device comprises a housing, a reservoir, a pump means, and a connector. The connector of the filling device is configured to mechanically connect to the connector of the pump device.

When the filling device and the pump device of the system according to the invention are connected to each other, the container and the reservoir are in fluid communication through the conduit.

When the trigger assembly of the system according to the invention is activated, liquid is expelled by the drive unit from the container through the conduit into the reservoir of the pump device.

In one embodiment of the system according to the invention, the pump device may further comprise a sensor configured to detect the fill level of the reservoir.

In a further embodiment of the system according to the invention the drive unit of the filling device is operated by a controller in expelling liquid from the container dependent on the signal from the sensor of the pump device such that the amount of liquid is adjusted to the fill level of the reservoir.

In another embodiment of the system according to the invention, the connector of the filling device is configured to identify a matching pump device.

In another embodiment of the system according to the invention, the reservoir of the pump device contains a lyophilized drug and the container of the filling device comprises a liquid solvent. The lyophilized drug may be inside the reservoir before the filling device is attached to the pump device. When the liquid solvent is expelled by the drive unit from the container through the conduit into the reservoir of the pump device, the lyophilized drug is dissolved and rendered a ready to use liquid medicament.

It is to be noted, that all features and embodiments as described herein are to be understood to equally apply to the drive mechanism, to the drug delivery device as well as to the method of operating the drug delivery device and its drive mechanism and to the computer program associated therewith. In particular, a mentioning of a component being configured or arranged to conduct a particular operation is to be understood to disclose a respective method or program step and vice versa.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu- Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the aforementioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the pertinent art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described by making reference to the drawings, in which.

DETAILED DESCRIPTION

Figure 1:
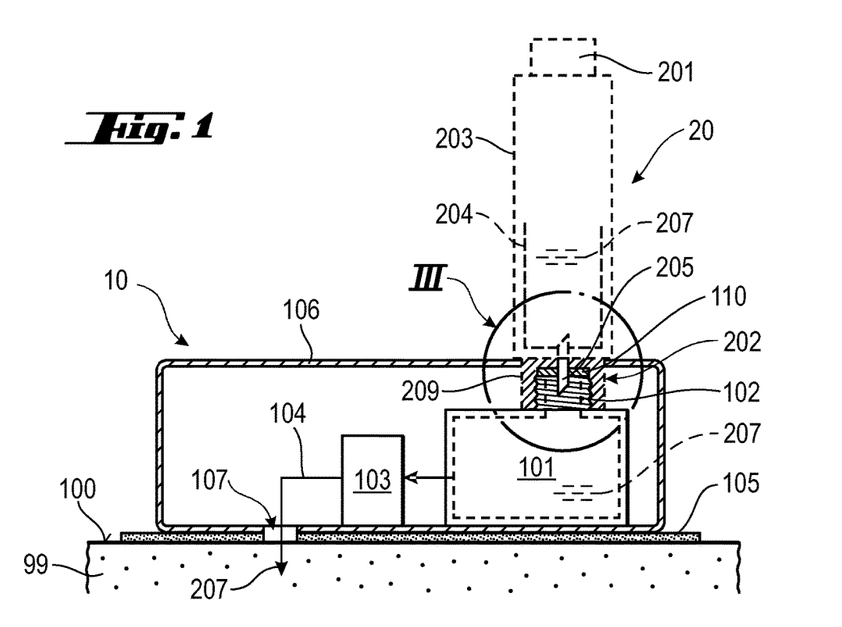
FIG. 1 schematically illustrates the configuration of a pump device with a filling device.

FIG. 1 shows a pump device comprising a housing 106 accommodating a medicament reservoir 101 and a pump mechanism 103 configured to deliver medicament 207 from the medicament reservoir 101 through a fluid connection 104 into a patient's body 99.

The pump device 10 is fixed to the patient's skin 100 by an adhesive tape 105 arranged at the bottom of the housing 106. The bottom of the housing 106 and the adhesive tape 105 have an aperture 107 to allow the fluid connection 104 to go through. A connecting element 102 is arranged on the top side of the housing 106 accessible to attach a connector 202 of a filling device 20.

Figure 2:
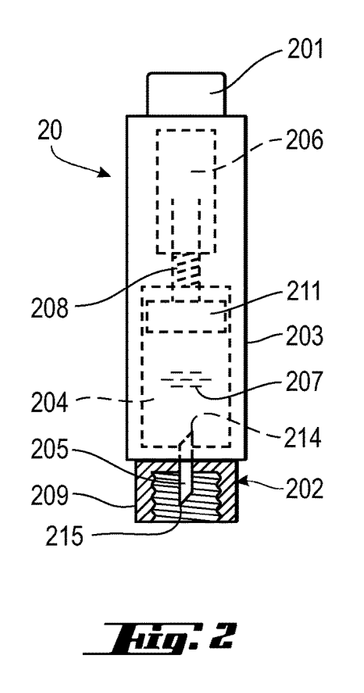
FIG. 2 illustrates a filling device according to a first embodiment.

FIG. 2 shows an embodiment of a filling device 20 according to the present invention.

The filling device 20 has an elongate shape and comprises a housing 203, a trigger assembly 201, a connector 202, and a needle cannula 205 serving as a conduit. The housing 203 serves to accommodate a drive unit 206 and a container, e.g. a cartridge 204.

The cartridge 204 has a piston 211 at one end and a septum (not shown) at the other end. The cartridge 204 is preferably filled with a liquid medicament 207. The needle cannula 205 has a sharp proximal end 214 suitable to pierce the septum of the cartridge 204. The drive unit 206 at least comprises a piston rod 208 to operably engage with the piston 211 of the cartridge 204. Once actuated by trigger assembly 201, the drive unit 206 acts on the piston 211 and medicament 207 contained in the cartridge 204 is expelled through the needle cannula 205.

The drive unit 206 is preferably implemented all-mechanically and comprises a spring arranged to act on the piston rod 208 once actuated by the trigger 201. The spring is a torsion spring or a compression spring. However, other stored energy means, such as gas springs or rubber bands, could be used.

The connector 202, in general, is configured to attach the filling device 20 to a drug reservoir 101 of a pump device 10 via connecting element 102.

Figure 3:
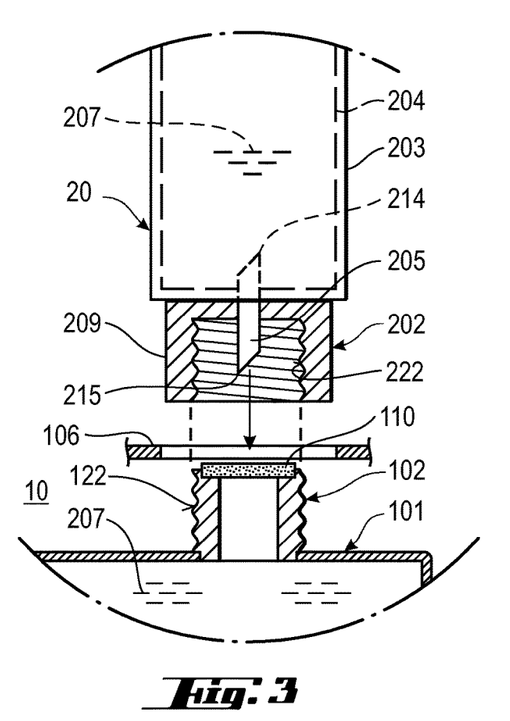
FIG. 3 shows an enlarged detail view of the connectors of the pump device in the area III of FIG. 1 and the filling device of FIG. 2.

FIG. 3 shows the connecting element 102 of the pump device 10 comprising a threading 122 that corresponds to the threading 222 of the connector 202 of the filling device 20. Alternatively, the connection may be a bayonet-like, or a snap fit connection. The connecting element 102 is shown attached to the reservoir 101. Alternatively, the connecting element 102 may be attached to the housing 106 however providing a fluid connection to the reservoir 101.

The connecting element 102 further comprises a sealing 110 that is pierced by a sharp distal end 215 of needle cannula 205 when the filling device 20 is attached to the medicament reservoir 101 of the pump device 10. The sealing is preferably made from rubber material to ensure that after detaching the filling device 20 the medicament reservoir 101 is sealed and protected against intrusion of bacteria, germs, dust, etc. Furthermore, the material is selected to allow multiple times attaching and detaching a filling device 20 to the pump device 10.

In order to prevent needle stick injury, the connector 202 comprises a sleeve 209 that is arranged to permanently extend beyond the distal end 215 of the needle cannula 205 in distal direction (arrow in FIG. 3).

Alternatively, the connector 202 could comprise a movable needle shield arrangement configured to be moveable relative to the needle cannula 205. However, the movable needle shield arrangement is arranged to permanently extend beyond the distal end of the needle cannula 205 in distal direction.

In a typical situation of use, a user needs to set up the pump device 10 for infusion of medicament, e.g. insulin. At first instance, the medicament reservoir 101 is empty. The filling device 20 has a cartridge 204 filled with the right liquid medicament 207. Preferably, the volume of cartridge 204 corresponds to the volume of the medicament reservoir 101.

The user would take the filling device 20, attach it to the reservoir 101 and press the trigger 201. Once actuated the drive unit 206 discharges the medicament 207 from the cartridge 204 through the needle cannula 205 into the medicament reservoir 101. The pump device 10 is now ready for use. Once the medicament reservoir 101 is empty, the user could take a new filling device 20 to refill the medicament reservoir 101.

This scenario could help the user to adhere to the filling and set-up procedure.

Having the same amount of medicament in the cartridge 204 and the medicament reservoir 101 should help preventing under- and/or overfilling. Hence this improves user comfort as well as it helps to prevent waste of medicament.

The filling device as described above typically is of disposable type. That is to say that after filling the reservoir 101 the filling device 20 is discarded.

Alternatively, the filling device 20 could be of re-usable type. That is to say that an empty cartridge 204 is replaced by a new cartridge 204 filled with medicament. This would immediately reduce waste. Further, this could help the user to adhere to the filling and set-up procedure.

In an alternative situation of use, a user needs to set up the pump device 10 for infusion of medicament. In difference to the situation described above, at first instance, the medicament reservoir 101 is filled with medicament in powdered or lyophilized state. Preferably, the lyophilized medicament is inside the reservoir before the filling device 20 is attached to the pump device 10. The filling device 20 has a cartridge 204 filled with the right liquid 207, which is a solvent in this situation. Preferably, the volume of cartridge 204 corresponds to the volume of the medicament reservoir 101. The user would take the filling device 20, attach it to the reservoir 101 and press the trigger 201. Once actuated the drive unit 206 discharges the liquid 207, i.e. the solvent in this situation, from the cartridge 204 through the needle cannula 205 into the medicament reservoir 101. The user then detaches the filling device 20 from the pump device 10 and may shake the pump device 10 a few times to make sure that the medicament is sufficiently dissolved. The pump device 10 is now ready for use.

This scenario could help the user to adhere to conditions where is it preferred to keep the pharmaceutically active substance in dry form up until before use. Thereby shelf live conditions could be improved.

In a further alternative situation of use, a user needs to clean the pump device 10. In a first step, the pump device needs to be sterilized before it can be filled with medicament. Alternatively, in a final step, the pump device may need to be sterilized after use in order to remove medicament residues. Therefore, the filling device 20 has a cartridge 204 filled with the right liquid 207, which is a sterilizing liquid in this situation.

This scenario could help the user to adhere to conditions where it is preferred to clean the pump device before and/or after use. For example, it might be advantageous to test the functionality of a pump device with a liquid that is cheaper than medicament. As another example it might be advantageous to remove medicament residues from a pump device after use, because the medicament may be hazardous for people not requiring this particular medicament. Therefore it might be beneficial to have the pump device filled with a sterilizing liquid before and/or after use with a medicament.

Figure 4:
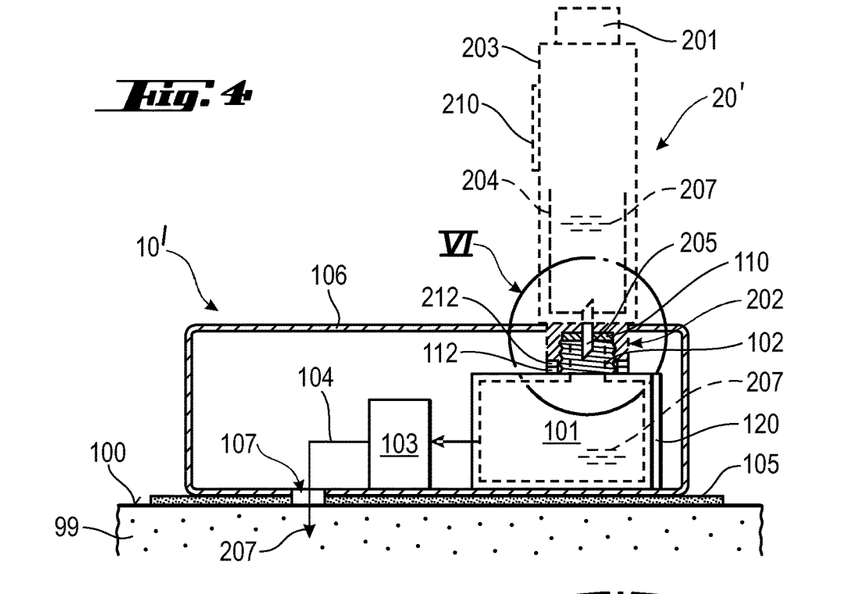
FIG. 4 illustrates another embodiment of a filling device and another pump device.

A further pump device 10' is shown in FIG. 4 which relates to another embodiment of a filling device 20' according to the invention.

The pump device 10' of FIG. 4 comprises the elements of the pump device 10 as described before. In addition, pump device 10' comprises a sensor 120 arranged to determine the fill level of the medicament reservoir 101. The pump device 10' further comprises a contact 112 connected to the sensor 120 arranged at the connecting element 102.

Figure 5:
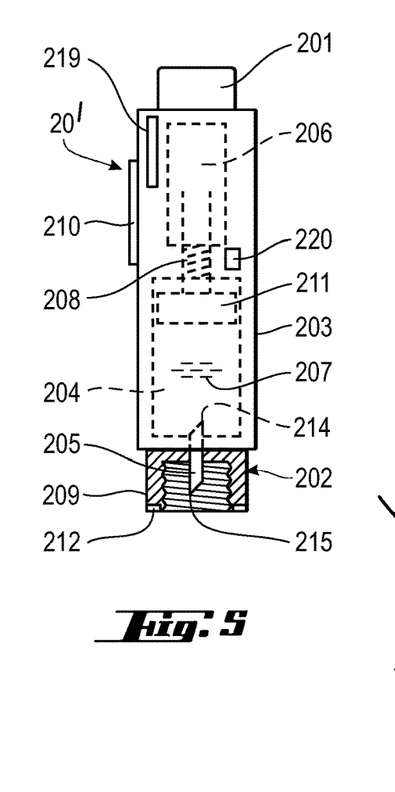
FIG. 5 illustrates another embodiment of a filling device.

A further embodiment of a filling device 20' according to the invention is shown in FIG. 5.

The filling device 20' of FIG. 5 comprises the elements known from filling device 20 as described before. In addition, the filling device 20' further comprises a contact element 212 and a display 210. The drive unit 206 of filling device 20' is implemented electromechanically, comprising at least a motor and gear assembly arranged to act on the piston rod 208, a battery 219 to provide power supply, and a controller 220 configured to at least control motor action. The controller 220 controls activation of the motor and gear arrangement 206 once actuated by trigger assembly 201. The trigger 201 assembly is implemented as a push button. The contact element 212 is electrically connected to the controller 220.

When the filling device 20' is attached to the pump device 10' the two devices can communicate via the contact element 212 and contact 112. For example, the fill level of the medicament reservoir 101 could be communicated to the controller 220 and the controller 220 commands the drive unit 206 to expel medicament 207 from the cartridge 204 dependent on the signal from the fill level sensor 120.

Figure 6:
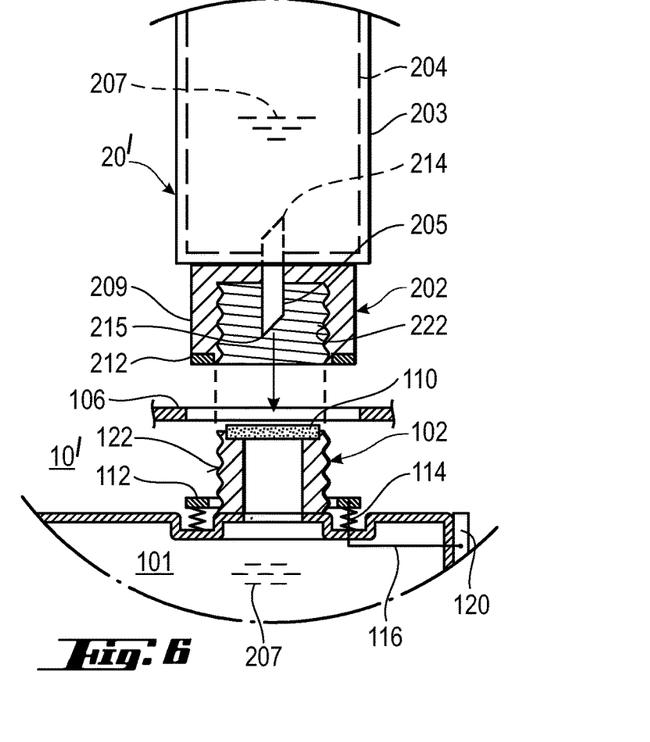
FIG. 6 shows an enlarged detail exploded view in the area VI of FIG. 4

FIG. 6 provides an enlarged detailed view of front or distal end of filling device 20' comprising the connector 202 comprising sleeve 209 and contact element 212. Also, a detailed enlarged view of the pump device 10' is provided showing the connecting element 102 including the sealing 110 and the contact 112. As can be seen, when connector 202 is attached to connecting element 102 contact element 212 is in contact with contact 112. Contact 112 may be biased by a spring 114 to ensure proper connection.

In a typical situation of use, a user would attach the filling device 20' to the pump device 10' to fill medicament 207 into the reservoir 101. The volume of the cartridge 204 does not have to correspond to the volume of the reservoir 101 because the flow of medicament from the cartridge 204 to the reservoir 101 is stopped once the fill level sensor 120 recognizes a certain fill level.

This further improves the handling of pump devices because such a system allows a user to fill up the reservoir 101 of the pump device 10' at any time convenient to the user. Further, in doing so, the user can make sure that he/she has the maximum amount of medicament available in the pump device.

In a further alternative embodiment (not shown) of the filling device, the conduit 205 is configured to be movable from a first state where it is not in fluid communication with the medicament container 204 to a second state, where it is in fluid communication with the medicament container 204. The conduit 205 is implemented as a double ended needle cannula fixed to a moveable hub. The hub is biased by a spring. The sleeve 209 comprises steps to delimit movement of the needle hub such that the conduit 205 can be moved form the first position against the biasing force of the spring to the second position. Once the filling device of this embodiment is attached to a pump device, the hub abuts connector element 102 and is moved against the force of the spring and the conduit is moved into the second position. The medicament 207 is in fluid communication with the conduit 205. Also, the conduit 205 is in fluid communication with the reservoir 101. Thereby it is ensured that the medicament 207 is expelled into the reservoir 101. When the filling device is not attached to the pump device, the hub does not abut the connector element 102 and is moved by the force of the spring in distal direction and the conduit 205 is moved into the first position. When the conduit 205 is not in fluid communication with the medicament 207, the medicament 207 in the container 204 is sealed and secured against intrusion of bacteria, germs, dust, etc. It is to be noted that this embodiment is particularly useful to be implemented in combination with any of the previous embodiments.

The invention claimed is:

1. A filling device for filling a drug reservoir of a pump device, the filling device comprising:
   a housing configured to hold a container for a liquid;
   a conduit arranged for fluid engagement with the container;
   a drive unit configured to expel the liquid from the container through the conduit;
   a connector configured to be attachable to the reservoir and comprising at least one contact element positioned at a distal end of the connector, wherein the at least one contact element is configured to enable transmission of signals to and from the filling device when the connector is attached to the reservoir and configured to disable transmission of signals to and from the filling device when the connector is detached from the reservoir;
   a trigger assembly arranged to act on the drive unit such that when the trigger assembly is activated, the liquid is expelled from the container through the conduit; and
   a controller configured to control activation of the drive unit, wherein the at least one contact element is electrically connected to the controller,
   wherein the drive unit is configured to expel the liquid from the container through the conduit dependent on a signal received from the pump device such that the amount of the liquid expelled from the container is based on a fill level of the drug reservoir.

2. The filling device of claim 1, wherein the connector further comprises a sleeve arranged to permanently extend beyond a distal end of the conduit in a distal direction.

3. The filling device of claim 1, wherein the drive unit comprises a stored-energy means configured to provide energy to expel the liquid from the container, and wherein the trigger assembly is configured to activate the stored-energy means.

4. The filling device of claim 1, wherein a distal end of the conduit comprises a sharp end adapted to pierce a seal of the reservoir.

5. The filling device of claim 2, wherein the sleeve is configured to mechanically connect to the reservoir.

6. The filling device of claim 1, wherein the connector is configured to provide a corresponding coupling arrangement with a matching reservoir.

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
        35

7. A system comprising:
the filling device according to claim 1; and
a pump device comprising a housing, the drug reservoir, a pump, and a connector; wherein the connector of the filling device is configured to mechanically connect to the connector of the pump device.

8. The system according to claim 7, wherein the pump device further comprises a sensor configured to detect a fill level of the reservoir.

9. The system according to claim 8, wherein the system is configured such that when the filling device is attached to the pump device, the container and the reservoir are in fluid communication through the conduit.

10. The system according to claim 8, wherein the system is configured such that when the trigger assembly is activated, the liquid is expelled by the drive unit from the container through the conduit and into the reservoir.

11. The system according to claim 9, wherein the pump device further comprises a contact connected to the sensor, the contact being located at or proximal to a connecting element, wherein the drive unit is configured to be operated by the controller in expelling the liquid from the container dependent on the signal from the sensor such that the amount of the liquid is based on the fill level of the reservoir.

12. The system according to claim 8, wherein the connector of the filling device is configured to provide a corresponding coupling arrangement with a matching pump device.

13. The filling device of claim 1 further comprising a piston rod configured to operably engage with a piston of the drug reservoir.

14. The filling device of claim 13, wherein the drive unit comprises a motor and gear assembly arranged to act on the piston rod.

15. The filling device of claim 3, wherein the stored-energy means comprises a spring.

* * * * *